United States Patent [19]

Drivon et al.

[11] Patent Number: 4,912,269

[45] Date of Patent: Mar. 27, 1990

[54] SYNTHESIS OF PERFLUOROALKYL BROMIDES

[75] Inventors: Gilles Drivon, Saint-Martin en Haut; Pierre Durual, Vernaison; Bernard Gurtner, Grenoble; André Lantz, Vernaison, all of France

[73] Assignee: Atochem, France

[21] Appl. No.: 214,201

[22] Filed: Jun. 28, 1988

[30] Foreign Application Priority Data

Jul. 10, 1987 [FR] France ............................ 87 09870

[51] Int. Cl.$^4$ ..................... C07C 17/22; C07C 19/08
[52] U.S. Cl. ...................................... 570/142; 570/137
[58] Field of Search ................. 570/142, 137; 260/694

[56] References Cited

U.S. PATENT DOCUMENTS 2,554,219  5/1951  Simons et al. ................... 570/142
3,456,024  7/1969  Loree .............................. 570/142

FOREIGN PATENT DOCUMENTS 512068  2/1968  France .

OTHER PUBLICATIONS

Kirk–Othmer, *Encyclopedia of Chemical Technology*, vol. 9, 2nd Ed.

*Primary Examiner*—J. E. Evans
*Attorney, Agent, or Firm*—Stevens, Davis, Miller & Mosher

[57] ABSTRACT

The invention relates to the preparation of perfluoroalkyl bromides or bromoperfluoroalkanes, $CnF_{2n+1}$-Br (n=1 to 20).

Gaseous hydrogen bromide is reacted with a perfluoroalkanesulphonyl chloride, $C_nF_{2n+1}$-$SO_2Cl$, in the presence of a catalyst consisting of a tertiary amine or phosphine or a quaternary ammonium or phosphonium salt, at a temperature ranging from 80° to 200° C.

7 Claims, No Drawings

SYNTHESIS OF PERFLUOROALKYL BROMIDES

FIELD OF THE INVENTION

The present invention concerns the field of perhalogenated aliphatic hydrocarbons. It relates more particularly to preparation of perfluoroalkyl bromides or bromoperfluoroalkanes, $R_f$-Br, $R_f$ denoting a linear or branched perfluoroalkyl radical, $C_nF_{2n+1}$, containing from 1 to 20 carbon atoms.

BACKGROUND OF THE INVENTION

These known compounds are used in numerous fields, in particular in medicine as radiopaque substances (X-ray contrast agents) or as oxygen transporters in blood substitutes. A compound which has been especially studied in this field is n-perfluorooctyl bromide, $C_8F_{17}Br$.

The following may be pointed out more particularly among the known methods for the preparation of these compounds:

the reaction of bromine wtth a compound $R_4$-$SF_5$ at 500° C. in the presence of nickel (U.S. Pat. No. 3,456,024), the gas-phase photolysis of a mixture of a 1-hydrogenperfluoroalkane and BrCl or BrF (Adcock et al, Chem. Abstr. 100: 34092 e), the reaction of bromine with the compounds $R_f$-I in the presence of a free-radical intiator such as AIBN (Japanese Application Kokai 85-184033), and the photobromination of these same iodine compounds by UV irradiation (Huang et al, Huaxue Xuebao, 42(10) 1106-8 (1984), abstracted in Chem Abstr. 102: 78312 x). The preceding references are hereby incorporated by reference.

The low yields obtained and/or the slow kinetics of these methods are such that they do not permit economic production of perfluoroalkyl bromides on an industrial scale. In view of the importance of these compounds in the medical field, it is of great interest to be able to manufacture them at the lowest possible cost.

SUMMARY OF THE INVENTION

A technique has now been found which makes it possible to manufacture perfluoroalkyl bromides in a single step, with an excellent yield and a very good selectivity, from the corresponding perfluoroalkane-sulphonyl chlorides, $R_f$-$SO_2Cl$. The process according to the invention, which corresponds to the following equation:

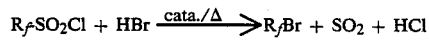

also offers numerous advantages over the existing methods, especially:

technological simplicity: use of conventional equipment (stirred reactor, moderate temperature, atmospheric pressure, etc.), fast kinetics, hence a high productivity capable of reaching about 0.5 mol/hour/liter of reactor, and operational reliability: simultaneous and controlled removal of hydrochloric acid and sulphur dioxide.

DETAILED DESCRIPTION OF THE INVENTION

The process according to the invention is characterized in that it comprises reacting gaseous hydrogen bromide with a perfluoroalkanesulphonyl chloride in the presence of a catalyst consisting of a tertiary amine or phosphine or a quaternary ammonium or phosphonium salt, at a temperature which can range from 80° to 200° C. and is preferably between 90° and 150° C. The optimum temperature depends on the number of carbon atoms of the starting sulphochloride and its purity. Thus, for example, it is about 120°-140° C. for freshly distilled $C_8F_{17}SO_2Cl$ and about 90°-120° C. for $C_6F_{13}SO_2Cl$.

The process according to the invention is preferably carried out at atmospheric pressure, but it would not be outside the framework of the invention to carry out the process under a slight positive or negative pressure. It can be carried out in a reactor fitted with conventional devices for stirring, heating and introducing gas and surmounted by a condenser joined to a device for recovering the waste gases (HCl, $SO_2$ and unconveted HBr).

The amount of catalyst to be used can vary within wide limits but is generally between 0.1 and 5 mol per 100 ml of perfluoroalkanesulphonyl cloride and preferably about 1 to 2 mol per 100 mol of perfluoroalkanesulphonyl chloride. Methyldioctylamine, triphenylphosphine and, more particularly, tetrabutylammonium bromide, methyltrioctylammonium chloride, dimethyldioctylammonium chloride, tetrabutylphosphonium bromide may be mentioned as examples of catalysts to be used according to the invention.

Although the reaction ca be carried out in a solvent which is inert towards hydrogen bromide, it is preferably carried out in the absence of a solvent, care being taken to ensure that the chosen reaction temperature is sufficient to liquify the reaction medium.

The flow rate of gaseous hydrogen bromide introduced into the reaction mixture comprising the perfluoroalkanesulphonyl chloride (preferably freshly distilled) and the catalyst, and heated to the appropriate temperature, can vary within wide limits. A fast flow rate favors the productivity while a slow flow rate favors the yield relative to the HBr used. An hourly flow rate of hydrogen bromide of the order of 0.1 to 0.5 mol per mol of perfluoroalkanesulphonyl chloride has proved particularly favorable, although this does not limit the field of the invention in any way. Whatever the chosen flow rate, the reaction is considered to be complete when $SO_2$ and HCl are no longer evolved in the waste gases.

EXAMPLES

The examples which follow illustrate the invention without implying a limitation.

EXAMPLE 1

282 g of crude perfluorooctanesulphonyl chloride (purity: 92%, i.e., 0.5 mol of $C_8F_{17}$-$SO_2Cl$) and 3.2 g (0.01 mol) of tetrabutylammonium bromide are placed in a 250 ml reactor equipped with a rotary stirrer (~500 rpm), a temperature connector, a gas injector and a cold-water condenser joined to a bubbler.

The mixture is heated to about 125° C. and gaseous hydrogen bromide is introduced at a rate of 0.13 mol/hour over a period of 4 and a half hours, with stirring. Quantitative analysis of the waste gases evolved indicates totals of 0.445 mol of HCl, 0.11 mol of HBr and 0.47 mol of $SO_2$.

The reaction medium is then degassed with nitrogen for one hour, after which it is filtered at room temperature to remove the supernatant solid. 250.5 g of a brick-red liquid are recovered in this way and shown by GC analysis to contain 0.47 mol of $C_8F_{17}Br$, i.e., a yield of 94%.

After removal of the residual acidity and distillation at atmospheric pressure (b.p.=146° C.), a product with a purity greater than 99.5% is obtained.

EXAMPLE 2

The procedure is the same as for Example 1 except that the tetrabutylammonium bromide is replaced with 3.4 g (0.01 mol) of tetrabutylphosphonium bromide.

This gives 250.2 g of a crude product containing 90.7% of $C_8F_{17}Br$, which can be purified as in Example 1.

EXAMPLE 3

The procedure is the same as for Example 1 except that the tetrabutylammonium bromide is replaced with 4 g (0.01 mol) of methyltrioctylammonium chloride (Aliquat 336) and the hydrogen bromide is introduced at a rate of 0.17 mol/hour over a period of 5 hours.

This gives 254 g of a crude product containing 0.43 mol of $C_8F_{17}Br$. Yield: 86%.

EXAMPLE 4

1847 g of $C_8F_{17}SO_2Cl$ with a GC purity of 90.5% (i.e., 3.22 mol of $C_8F_{17}SO_2Cl$) and 22.4 g of tetrabutylammonium bromide are charged into a 2-liter reactor equipped with a mechanical stirrer, a temperature connector, a gas injection pipe and a reflux condenser joined to a water column for recovering the waste gases.

The reaction mixture is heated to about 125° C. and anhydrous HBr is introduced at a rate of 1 mol/hour over a period of 4 hours.

After degassing with nitrogen for 1 hour and removal of the supernatant solid by filtration at room temperature, a brick-red liquid weighing 1730 g and having a GC purity of 88.5% is recovered, i.e., 3.07 mol of $C_8F_{17}Br$, which corresponds to a yield of 95%.

A product with a purity of $\geq$ 99.5% is collected by distillation of this crude reaction product at atmospheric pressure.

Quantitative analysis of the waste gases evolved during the reaction indicates totals of 3.09 mol of HCl and 2.90 mol of $SO_2$.

EXAMPLE 5

The procedure is the same as for Example 1 except that the tetrabutylammonium bromide is replaced with 2.5 g (0.01 mol) of methyldioctylamin.

This gives 256.5 g of a crude product containing 61.5% of $C_8F_{17}Br$. Yield: 63%.

EXAMPLE 6

The procedure is the same as for Example 1 except that the tetrabutylammonium bromide is replaced with 2.6 g (0.01 mol) of triphenylphosphine.

This gives 278 g of crude product containing 57% of $C_8F_{17}Br$. Yield: 64%.

EXAMPLE 7

251 g of freshly distilled perfluorohexanesulphonyl chloride (purity : 99.4%; i.e., 0.6 mol of $C_6F_{13}SO_2Cl$) and 3.9 g of tetrautylammonium bromide are placed in the same apparatus as for Example 1.

The reaction mixture is heated to 120° C. and anhydrous HBr is then introduced for 5 hours at a rate between 0.3 and 0.1 mol/hour. The temperature of the reaction medium stabilizes rapidly at 95–100° C. due to refluxing of the $C_6F_{13}Br$ formed. Analysis of the waste gases indicates a total releasing of 0.58 mol of HCl, 0.575 mol of $SO_2$ and 0.68 mol of HBr.

After degassing with nitrogen for one hour and decanting the catalyst, 229 g of organic phase are recovered which contains 96.8% of $C_6F_{13}Br$, that is a yield of 92.6%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A process for the preparation of perfluoroalkyl bromides, comprising reacting gaseous hydrogen bromide with a perfluoroalkane sulphonyl chloride in the presence of a catalyst consisting of a tertiary amine or phosphine or a quaternary ammonium or phosphonium salt, at a reaction temperature ranging from 80° to 200° C. recovering perfluoralkyl bromide.

2. The process according to claim 1, wherein 0.1 to 5 mol of catalyst are used per 100 mol of perfluoroalkanesulphonyl chloride.

3. The process according to claim 2, wherein about 1 to 2 mol of catalyst are used per 100 mol of perfluoroalkane sulphonyl chloride.

4. The process according to claim 1, wherein the catalyst is tetrabutylammonium bromide, methyltrioctylammonium chloride, dimethyldioctylammonium chloride or tetrabutylphosphonium bromide.

5. The process according to claim 1, wherein the reaction temperature is between 90° and 150° C.

6. The process according to claim 1, wherein the hourly flow rate of hydrogen bromide is about 0.1 to 0.5 mol per mol of perfluoroalkanesulphonyl chloride.

7. The process according to claim 1, wherein perfluorooctanesulphonyl chloride is used as the starting material to form perfluorooctyl bromide.

* * * * *

UNITED STATES PATENT AND TRADEMARK OFFICE
CERTIFICATE OF CORRECTION

PATENT NO. : 4,912,269
DATED : March 27, 1990
INVENTOR(S) : DRIVON, et al.

It is certified that error appears in the above-identified patent and that said Letters Patent is hereby corrected as shown below:

On title page of the patent, under "FOREIGN PATENT DOCUMENTS", change the patent number of the French reference from "512068" to --1512068--.

Column 1, line 22, change "$R_4-SF_5$" to --$R_f-SF_5$--.

Column 2, line 23, change "ml" to --mol--.

Column 2, line 31, change "ca" to --can--.

Column 4, line 12, change "tetrautylammonium" to --tetrabutylammonium--.

Column 4, Claim 1, line 39, after "C.", insert --and--.

Signed and Sealed this

Sixteenth Day of July, 1991

Attest:

HARRY F. MANBECK, JR.

Attesting Officer     Commissioner of Patents and Trademarks